(12) United States Patent
    Flores

(10) Patent No.: US 8,418,796 B2
(45) Date of Patent: Apr. 16, 2013

(54) BREATHALYZER MASKING DEVICE

(75) Inventor: Alethea Veronica Flores, Round Rock, TX (US)

(73) Assignee: Alethea Flores, Round Rock, TX (US)

( * ) Notice: Subject to any disclaimer, the term of this patent is extended or adjusted under 35 U.S.C. 154(b) by 0 days.

(21) Appl. No.: 13/385,716

(22) Filed: Mar. 1, 2012

(65) Prior Publication Data
    US 2012/0244371 A1    Sep. 27, 2012

Related U.S. Application Data

(60) Provisional application No. 61/448,052, filed on Mar. 1, 2011.

(51) Int. Cl.
    *B60K 28/06* (2006.01)

(52) U.S. Cl.
    USPC ............. 180/272; 600/632; 340/576; 422/84; 206/305; 206/306

(58) Field of Classification Search .................. 180/272; 600/532; 73/23.3; 422/84; 340/426.11, 340/576; 206/305, 306, 523, 217, 320, 438
    See application file for complete search history.

(56) References Cited

U.S. PATENT DOCUMENTS 6,123,198  A  *  9/2000  Pflueger et al. ............... 206/581
    2003/0052692 A1*  3/2003  Lin ............................. 324/464
    2012/0031166 A1*  2/2012  Lopez et al. ................. 73/23.3
    2012/0048753 A1*  3/2012  Johnson-Griggs ............ 206/305

* cited by examiner

*Primary Examiner* — Ruth Ilan

(57) ABSTRACT

A breathalyzer masking device for concealment of vehicle installed breathalyzer devices.

4 Claims, 1 Drawing Sheet

Product disguises breathalyser installed in vehicle

BREATHALYZER MASKING DEVICE

BACKGROUND OF THE INVENTION

1. Field of the Invention

The present invention relates generally to the field of breathalyzers and more specifically relates to a breathalyzer masking device.

2. Description of the Related Art

A common problem in modern society, due to the ready availability of alcoholic beverages and modern societal pressures, many individuals drive a motor vehicle while being intoxicated. Driving under the influence (driving while intoxicated) is the act of operating any motorized machinery during or after consuming alcohol or other drugs. DUI or DWI are synonymous terms that represent the criminal offense of operating (or in some jurisdictions merely being in physical control of) a motor vehicle while being under the influence of alcohol or drugs or a combination of both. Operating vehicles under the influence of alcohol or drugs is a criminal offense in most countries.

A method largely employed for both limiting and monitoring an offender's driving is an ignition interlock device. According to information provided by the Alcohol Interlock Symposium, an international organization that promotes widespread use of the device, an ignition interlock device or breath alcohol ignition interlock device is a mechanism, like a breathalyzer, installed onto a motor vehicle's dashboard. Before the motor can be started, the driver must first exhale into the device; if the resulting breath-alcohol concentration result is greater than the programmed blood alcohol concentration (typically between 0.02% or 0.04%, or whatever the legal limit is in a particular state) the device prevents the engine from being started. The devices keep a record of the activity on the device and the interlocked vehicle's electrical system. This log is printed out or downloaded each time the device's sensors are calibrated, commonly at 30, 60, or 90 day intervals. Authorities may require periodic review of the log, and if violations are detected, then additional sanctions can be implemented. While debates rage on the effectiveness of this practice, as it pertains to rehabilitation efforts, one thing is certain: those who are forced to use a breath alcohol interlock device are rightfully humiliated by the procedure. Whether sitting in their driveway, getting ready to leave work, or preparing to back out of a grocery store parking space, these individuals are in full view of passerby as they exhale into the breathalyzer. The act of individuals watching may cause shame upon the driver and loss of reputation which may have negative effects not intended by the punishment, for example loss of business or other.

Various attempts have been made to solve problems found in breathalyzer art. Among these are found in: U.S. Pat. No. 7,377,186 to Duval; U.S. Pat. No. 7,413,047 to Brown; and U.S. Pat. No. 2005/0087382 to Bellehumeur. This prior art is representative of alcohol impairment detection devices.

Alcohol impairment detection devices that, have been installed on vehicles detect the presence of ethanol in the driver's breath to prevent accidents. These devices tend to mark an individual as an "alcoholic" and can be embarrassing or even stigmatize the person. A breathalyzer masking device is needed to avoid the embarrassment. None of the above inventions and patents, taken either singly or in combination, is seen to describe the invention as claimed. Thus, a need exists for a reliable breathalyzer masking device to avoid embarrassment and the above-mentioned problems, yet still provide safety and justice for the general public.

BRIEF SUMMARY OF THE INVENTION

In view of the foregoing disadvantages inherent in the known breathalyzer art, the present invention provides a novel breathalyzer masking device. The general purpose of the present invention, which will be described subsequently in greater detail, is to provide concealment of vehicle installed breathalyzer devices. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and method(s) of use for the present invention, Mask It, constructed and operative according to the teachings of the present invention.

The various embodiments of the present invention will hereinafter be described in conjunction with the appended drawings.

DETAILED DESCRIPTION

As discussed above, embodiments of the present invention relate to a breathalyzer device and more particularly to a breathalyzer masking device as used to conceal the presence of breathalyzer devices.

Figure 1:
FIG. 1 shows a perspective view illustrating a breathalyzer masking device according to an embodiment of the present invention.
Figure 2:
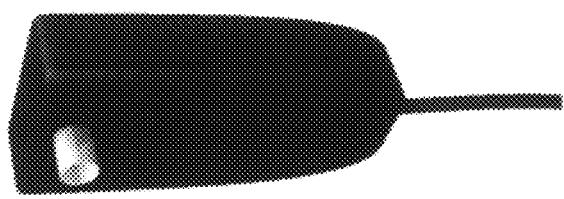
FIG. 2 is a perspective view illustrating a vehicle installed breathalyzer according to an embodiment of the present invention.

Referring now to the drawings FIGS. 1-2, the Mask essentially provides a "disguise" that is specially designed to mask breathalyzer equipment installed in vehicles. The Mask may be offered in a variety of designs, all with the intended purpose of rendering the breathalyzer as another object altogether. One very clever disguise comprises a "costume" of a Styrofoam or plastic cup with straw, similar in appearance to a to-go soda cup one can purchase in any convenience store. This facade would be constructed to completely sheathe a breathalyzer without compromising its operation. As such the cup part can wrap around the handle part of the equipment, and the "straw" strategically placed next to the mouthpiece of the device. In this manner, when a user has to exhale into the breathalyzer in order to start the car, it will appear to everyone within view that the motorist is enjoying a sip of a cool refreshing beverage. As such, the product would be produced in two separate hollow pieces. After placing both halves around the breathalyzer, it would snap into place. A foam insert may be used to ensure a snug fit and hold the breathalyzer in place. A hole located below the fake straw allows the mouthpiece to slightly protrude and be utilized. A hole located at the bottom of the cup allows the power cord to exit. Other disguises offered may include a hair cover that could blend the device with a female driver's own hair, or a faux hand holding a cigar or water bottle. With such a creative product, the possibilities for disguises are virtually limitless. Employing the Mask It, individuals who have been convicted of drunk driving can accept their punishments without the attendant embarrassment of revealing it to others.

Importantly, these disguises according to the present invention would eliminate the temptation to cower down in a moving vehicle should it become necessary to exhale into the breathalyzer to keep it running; casually "taking a sip" from a "straw" could prevent a serious traffic accident. Fully developed and affordably priced, the unique Mask It would be well received by the niche market of consumers who are forced to use a breath alcohol ignition interlock device, and who wish to preserve their reputations.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

The invention claimed is:

1. A breathalyzer masking device comprising:
    a hollow housing configured to resemble a beverage cup and containing a breath alcohol analyzer therein; said hollow housing configured to completely sheath the breath alcohol analyzer and including a hole located on a side of the hollow housing which is configured to receive a mouthpiece of the breath alcohol analyzer and allow the mouthpiece to protrude from the housing;
    a lid located on top of the hollow housing;
    a straw protruding from the lid and strategically located next to the mouthpiece;
    wherein an end of the straw is located adjacent the mouthpiece such that a user exhaling into the mouthpiece would appear to be sipping from the straw.

2. The breathalyzer masking device of claim 1, further including a hole located in the bottom of the hollow housing that allows a power cord of the breath alcohol analyzer to exit.

3. The breathalyzer masking device of claim 1, wherein the hollow housing is formed from two pieces and snapped together.

4. The breathalyzer masking device of claim 1, wherein a foam insert is located in the hollow housing.

* * * * *